US010729338B2

(12) United States Patent
Wang et al.

(10) Patent No.: US 10,729,338 B2
(45) Date of Patent: Aug. 4, 2020

(54) BLOOD PRESSURE MEASUREMENT DEVICE AND CALIBRATION METHOD THEREOF

(71) Applicant: BOE TECHNOLOGY GROUP CO., LTD., Beijing (CN)

(72) Inventors: Guohe Wang, Beijing (CN); Hui Du, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 204 days.

(21) Appl. No.: 15/565,770

(22) PCT Filed: May 22, 2017

(86) PCT No.: PCT/CN2017/085299
§ 371 (c)(1),
(2) Date: Oct. 11, 2017

(87) PCT Pub. No.: WO2018/058979
PCT Pub. Date: Apr. 5, 2018

(65) Prior Publication Data
US 2018/0279888 A1    Oct. 4, 2018

(30) Foreign Application Priority Data

Sep. 28, 2016   (CN) .......................... 2016 1 0862534

(51) Int. Cl.
 *A61B 5/1455*   (2006.01)
 *A61B 5/0205*   (2006.01)
 (Continued)

(52) U.S. Cl.
 CPC ........ *A61B 5/02233* (2013.01); *A61B 5/0002* (2013.01); *A61B 5/022* (2013.01);
 (Continued)

(58) Field of Classification Search
None
See application file for complete search history.

(56) References Cited

U.S. PATENT DOCUMENTS

| 2002/0143259 A1 | 10/2002 | Stergiopoulos et al. | |
| 2006/0074322 A1* | 4/2006 | Nitzan | A61B 5/021 600/485 |
| 2010/0249617 A1* | 9/2010 | Leung | A61B 5/022 600/495 |

FOREIGN PATENT DOCUMENTS

| CN | 1548005 A | 11/2004 |
| CN | 1849998 A | 10/2006 |

(Continued)

OTHER PUBLICATIONS

International Search Report & Written Opinion dated Jul. 25, 2017, regarding PCT/CN2017/085299.

(Continued)

*Primary Examiner* — Eric F Winakur
*Assistant Examiner* — Marjan Fardanesh
(74) *Attorney, Agent, or Firm* — Intellectual Valley Law, P.C.

(57) ABSTRACT

The present application discloses a blood pressure measurement device, includes: a blood pressure measurement body configured to measure blood pressure based on photoplethysmogram (PPG); and a calibrator configured to measure blood pressure values based on Korotkoff sounds. The calibrator is further configured to provide initial calibration parameters to the blood pressure measurement body, and the blood pressure measurement body is further configured to collect an ECG signal and a PPG signal, calibrate a PPG parameter-blood pressure equation according to the initial calibration parameters, and calculate a blood pressure value according to the PPG parameter-blood pressure equation.

15 Claims, 3 Drawing Sheets

(51) Int. Cl.
  *A61B 5/0402* (2006.01)
  *A61B 5/022* (2006.01)
  *A61B 5/00* (2006.01)
  *A61B 5/024* (2006.01)
  *A61B 5/021* (2006.01)
  *A61B 5/04* (2006.01)
  *A61B 5/0225* (2006.01)
  *A61B 5/025* (2006.01)

(52) U.S. Cl.
  CPC .......... *A61B 5/0205* (2013.01); *A61B 5/0225* (2013.01); *A61B 5/02108* (2013.01); *A61B 5/02416* (2013.01); *A61B 5/0402* (2013.01); *A61B 5/04012* (2013.01); *A61B 5/681* (2013.01); *A61B 5/6824* (2013.01); *A61B 5/6826* (2013.01); *A61B 5/7271* (2013.01); *A61B 5/0004* (2013.01); *A61B 5/025* (2013.01); *A61B 2560/0223* (2013.01); *A61B 2562/221* (2013.01)

(56) References Cited

FOREIGN PATENT DOCUMENTS

| | | |
|---|---|---|
| CN | 101229058 A | 7/2008 |
| CN | 101327121 A | 12/2008 |
| CN | 101884526 A | 11/2010 |
| CN | 102488503 A | 6/2012 |
| CN | 104257371 A | 1/2015 |
| CN | 105595979 A | 5/2016 |
| CN | 105748051 A | 7/2016 |
| CN | 105943005 A | 9/2016 |
| JP | 2002172094 A | 6/2002 |

OTHER PUBLICATIONS

First Office Action in the Chinese Patent Application No. 201610862534.4, dated May 27, 2019; English translation attached.

* cited by examiner

BLOOD PRESSURE MEASUREMENT DEVICE AND CALIBRATION METHOD THEREOF

CROSS-REFERENCE TO RELATED APPLICATION

This application is a national stage application under 35 U.S.C. § 371 of International Application No. PCT/CN2017/085299, filed May 22, 2017, which claims priority to Chinese Patent Application No. 201610862534.4, filed Sep. 28, 2016, the contents of which are incorporated by reference in the entirety.

TECHNICAL FIELD

The present disclosure generally relates to the technical field of medical device and, more particularly, relates to a blood pressure measurement device and a calibration method thereof.

BACKGROUND

Blood pressure is an important parameter that reflects the reproductive health conditions of human bodies. Particularly, for middle-aged or elderly patients with cardiovascular disease, frequent blood pressure measurements may have a vital role in disease warning, management, and treatment. As a country gradually develops into an aging society, the number of people suffers from high blood pressure (also called hypertension) increases constantly, and the market size of home-based blood pressure monitors expands continuously.

A conventional non-invasive blood pressure monitor includes a cuff-type blood pressure monitor. However, the cuff-type blood pressure monitor is not easy to use, and frequent use of the cuff-type blood pressure monitor may squeeze blood vessels and tissues under the cuff to cause discomfort. Simultaneously, because being hard to miniaturize and carry with, the cuff-type blood pressure monitors often fail to satisfy the measurement demands requested anytime by hypertensive patients.

Some blood pressure measurements may be cuff-less and may include wearable devices, where the blood-pressure measurement is based on photoplethysmography (PPG, a method of measuring pulse waves) signals and electrocardiogram (ECG) signals. The PPG method, however, is lack of measurement accuracy, needs a complicated calibration for each individual when in use, and requires re-calibration every once a while.

As such, there is a need to realize accurate measurements and to improve conveniences in use of the blood pressure monitor. The disclosed devices and methods are directed to solve one or more problems set forth above and other problems.

SUMMARY

One aspect of the present disclosure provides a display a blood pressure measurement device, including: a blood pressure measurement body configured to measure blood pressure based on photoplethysmogram (PPG); and a calibrator configured to measure blood pressure values based on Korotkoff sounds. The calibrator is further configured to provide initial calibration parameters to the blood pressure measurement body, and the blood pressure measurement body is further configured to collect an ECG signal and a PPG signal, calibrate a PPG parameter-blood pressure equation according to the initial calibration parameters, and calculate a blood pressure value according to the PPG parameter-blood pressure equation.

Optionally, the blood pressure measurement body further includes an ECG acquisition device, a PPG acquisition device, a storage device, a first processor, and a first communication device; the ECG acquisition device is coupled to the first processor, and configured to collect and transmit the ECG signal to the first processor; the PPG acquisition device is coupled to the first processor, and configured to collect and transmit the PPG signal to the first processor; the storage device is coupled to the first processor, and configured to store a PPG parameter and the PPG parameter-blood pressure equation; and the first processor is configured to process the ECG signal and the PPG signal, extract and calculate the PPG parameter in a cardiac cycle when receiving a systolic pressure notification signal and when receiving a diastolic pressure notification signal, transmit the PPG parameter of the cardiac cycle, and calculate the blood pressure value according to the PPG parameter-blood pressure equation.

Optionally, the calibrator includes a cuff, a sound transducer, a pressure gage, a second processor, and a second communication device, the sound transducer is configured to detect and convert a blood flow sound to an electric signal, the pressure gage is configured to measure a pressure inside the cuff, the second processor is configured to process the electric signal, and extract the Korotkoff sounds appeared in a blood flow sound and the pressure inside the cuff at the instances that the Korotkoff sounds correspond to the systolic pressure and the diastolic pressure, and the second communication device is coupled to the second processor, and configured to send a systolic pressure notification signal and a diastolic pressure notification signal, the systolic pressure and the diastolic pressure to the blood pressure measurement body, respectively, at the moments that the Korotkoff sounds correspond to the systolic pressure and the diastolic pressure.

Optionally, the second communication device includes a receiving device that matches with the first communication device.

Optionally, communications between the first communication device and the second communication device include a wired communication or a wireless communication.

Another aspect of the present disclosure provides a blood pressure measurement body, the blood pressure measurement body measuring blood pressure based on photoplethysmogram (PPG) and performing calibration based on blood pressure values based on Korotkoff sounds. The blood pressure measurement body is configured to collect an ECG signal and a PPG signal, calibrate a PPG parameter-blood pressure equation according to the initial calibration parameters based on Korotkoff sounds, and calculate a blood pressure value according to the PPG parameter-blood pressure equation.

Optionally, the blood pressure measurement body includes an ECG acquisition device, a PPG acquisition device, a storage device, a first processor, and a first communication device, the ECG acquisition device is coupled to the first processor, and configured to collect and transmit the ECG signal to the first processor, the PPG acquisition device is coupled to the first processor, and configured to collect and transmit the PPG signal to the first processor, the storage device is coupled to the first processor, and configured to store a PPG parameter and the PPG parameter-blood pressure equation, and the first processor is configured to process the ECG signal and the PPG signal, extract and calculate the PPG parameter in a cardiac cycle when receiving a systolic pressure notification signal and when receiving a diastolic pressure notification signal, transmit the PPG parameter of the cardiac cycle, and calculate the blood pressure value according to the PPG parameter-blood pressure equation.

Optionally, the blood pressure measurement body is coupled to a calibrator. The calibrator includes a cuff, a sound transducer, a pressure gage, a second processor, and a second communication device, the sound transducer is configured to detect and convert a blood flow sound to an electric signal, the pressure gage is configured to measure a pressure inside the cuff, the second processor is configured to process the electric signal, and extract the Korotkoff sounds appeared in a blood flow sound and the pressure inside the cuff at the moments that the Korotkoff sounds correspond to the systolic pressure and the diastolic pressure, and the second communication device is coupled to the second processor, and configured to send a systolic pressure notification signal and a diastolic pressure notification signal, the systolic pressure and the diastolic pressure to the blood pressure measurement body, respectively, at the moments that the Korotkoff sounds correspond to the systolic pressure and the diastolic pressure.

Another aspect of the present disclosure provides a calibration method of a blood pressure measurement device, including: measuring a PPG signal and an ECG signal and calculating PPG parameters, by a blood pressure measurement body. The PPG parameters include a PPG transmission time and a PPG peak-to-valley ratio; inflating a calibrator; deflating the calibrator, and when a systolic pressure is detected, sending a systolic pressure notification signal and a systolic pressure at a first instance to the blood pressure measurement body; after receiving, by the blood pressure measurement body, the systolic pressure notification signal, determining a cardiac cycle that the first instance belongs to, and calculating and recording the PPG parameters in a same cardiac cycle as the systolic pressure. The PPG parameters at least include the PPG transmission time. When a diastolic pressure is detected, sending a diastolic pressure notification signal and a diastolic pressure at a second instance to the blood pressure measurement body; after receiving, by the blood pressure measurement body, the diastolic pressure notification signal, determining the cardiac cycle that the second instance belongs to, and calculating and recording the PPG parameters in the same cardiac cycle as the diastolic pressure, wherein the PPG parameters at least include the PPG peak-to-valley ratio, and updating a PPG parameter-blood pressure equation according to the PPG transmission time and the PPG peak-to-valley ratio.

Optionally, the systolic pressure is determined as: $SBP = a \cdot (x-x_0) + SBP_0$, and the diastolic pressure is determined as:

$$DBP = b \cdot DBP_0 \cdot \frac{y_0}{y} + c.$$

Optionally, the $SBP_0$ is the initial systolic pressure; $x_0 = PTT_0$ or $x_0 = \overline{PTT_0}$; $PTT_0$ and $\overline{PTT_0}$ are an initial PPG transmission time and an average initial PPG transmission time, respectively; $x = PTT$ or $x = \overline{PTT}$, PTT and $\overline{PTT}$ are a PPG transmission time and an average PPG transmission time, respectively; and a is a statistic constant, and $DBP_0$ is the initial diastolic pressure; $y_0 = PIR_0$ or $y_0 = \overline{PIR_0}$; $PIR_0$ and $\overline{PIR_0}$ are an initial PPG peak-to-valley ratio and an average initial PPG peak-to-valley ratio, respectively; $y = PIR$ or $y = \overline{PIR}$, PIR and $\overline{PIR}$ are a PPG peak-to-ratio and an average PPG peak-to-ratio, respectively; and b and c are statistic constants.

Optionally, the PPG transmission time is a PPG transmission time in a single cardiac cycle, or an average value of PPG transmission time in a plurality of cardiac cycles, and the PPG peak-to-valley ratio is a PPG peak-to-valley ratio in a single cardiac cycle, or an average value of PPG peak-to-valley ratios in a plurality of cardiac cycles.

Optionally, a limb of the tested user where the blood pressure measurement body is placed is a wrist, a finger, or an arm, and another limb of the tested user where the calibrator is placed is an arm.

Optionally, communications between the blood pressure measurement body and the calibrator include a wired communication or a wireless communication.

Another aspect of the present disclosure provides a calibration method of a blood pressure measurement device, including: measuring a PPG signal and an ECG signal and calculating PPG parameters, by the blood pressure measurement body. The PPG parameters include a PPG transmission time and a PPG peak-to-valley ratio. When a systolic pressure is detected by a calibrator, receiving a systolic pressure notification signal and a systolic pressure at a first instance; determining a cardiac cycle that the first instance belongs to, and calculating and recording the PPG parameters in a same cardiac cycle as the systolic pressure, wherein the PPG parameters at least include the PPG transmission time; when a diastolic pressure is detected by the calibrator, receiving a diastolic pressure notification signal and a diastolic pressure at a second instance; determining the cardiac cycle that the second instance belongs to, and calculating and recording the PPG parameters in the same cardiac cycle as the diastolic pressure, wherein the PPG parameters include the PPG peak-to-valley ratio, and updating a PPG parameter-blood pressure equation according to the PPG transmission time and the PPG peak-to-valley ratio.

Optionally, the systolic pressure is determined as: $SBP = a \cdot (x-x_0) + SBP_0$, and the diastolic pressure is determined as:

$$DBP = b \cdot DBP_0 \cdot \frac{y_0}{y} + c.$$

The $SBP_0$ is the initial systolic pressure; $x_0 = PTT_0$ or $x_0 = \overline{PTT_0}$; $PTT_0$ and $\overline{PTT_0}$ are an initial PPG transmission time and an average initial PPG transmission time, respectively; $x = PTT$, or $x = \overline{PTT}$, PTT and $\overline{PTT}$ are a PPG transmission time and an average PPG transmission time, respectively; and a is a statistic constant, and $DBP_0$ is the initial diastolic pressure; $y_0 = PIR_0$ or $y_0 = \overline{PIR_0}$; $PIR_0$ and $\overline{PIR_0}$ are an initial PPG peak-to-valley ratio and an average initial PPG peak-to-valley ratio, respectively; $y = PIR$ or $y = \overline{PIR}$, PIR and $\overline{PIR}$ are a PPG peak-to-ratio and an average PPG peak-to-ratio, respectively; and b and c are statistic constants.

Optionally, the PPG transmission time is a PPG transmission time in a single cardiac cycle, or an average value of PPG transmission time in a plurality of cardiac cycles, and the PPG peak-to-valley ratio is a PPG peak-to-valley ratio in a single cardiac cycle, or an average value of PPG peak-to-valley ratios in a plurality of cardiac cycles.

BRIEF DESCRIPTION OF THE FIGURES

The following drawings are merely examples for illustrative purposes according to various disclosed embodiments and are not intended to limit the scope of the present invention.

In the accompanying drawings.

1. Blood pressure measurement body; 11. ECG acquisition device; 12. PPG acquisition device; 13. Storage device; 14. First processor; 15. First communication device; 16. Watch strap.

2. Calibrator, 21. Sound transducer; 22. Pressure gage; 23. Second processor; 24. Second communication device; 25. Cuff.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Embodiment 1

The present disclosure provides a blood pressure measurement device. The blood pressure measurement device may implement auto-calibrated blood pressure measurement based on the PPG principle, thereby effectively solving issues that calibration needs to be performed for each individual when using the blood pressure monitor based on the PPG. Accordingly, the measurement accuracy may be ensured and the blood pressure measurement device based on PPG may be used conveniently. In the present disclosure, a blood pressure measurement device may be a blood pressure measuring wrist band coupled with a blood pressure measuring cuff. The blood pressure measuring wrist band may calibrate itself base on the readings from the blood pressure measuring cuff. The blood pressure measuring cuff may be referred to as a calibrator 2.

Figure 1:
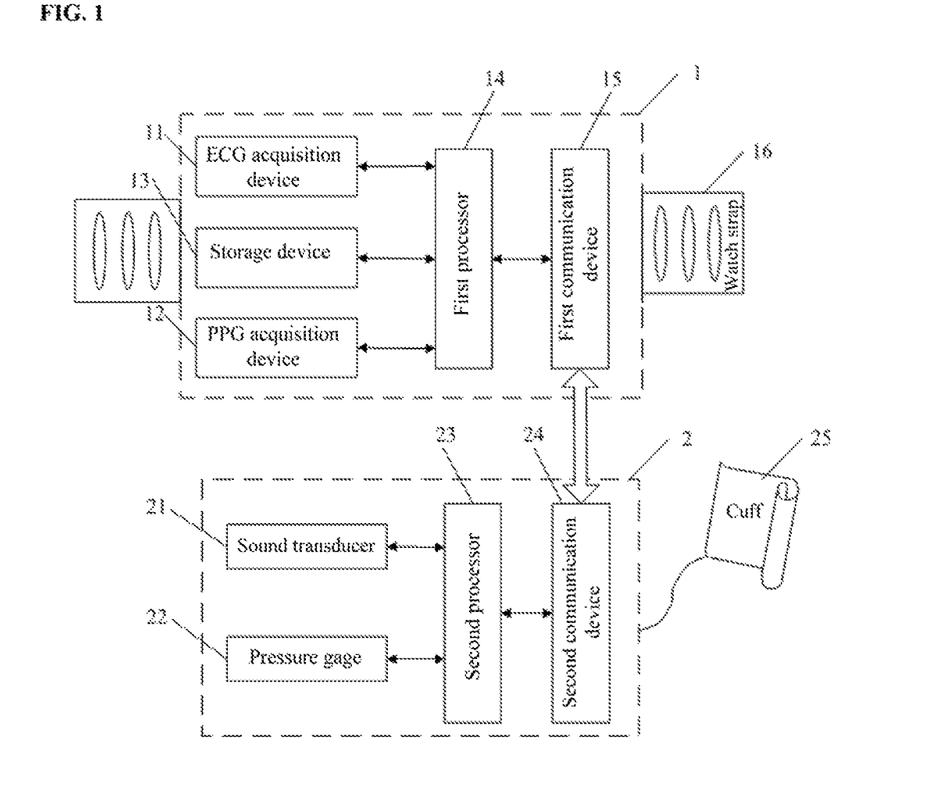
FIG. 1 is a diagram illustrating a schematic view of an exemplary blood pressure measurement device in some embodiments.

FIG. 1 is a diagram illustrating a schematic view of an exemplary blood pressure measurement device in some embodiments. As shown in FIG. 1, the blood pressure measurement device includes a blood pressure measurement body 1, and a calibrator 2. The blood pressure measurement body is configured to perform blood pressure measurement based on PPG and perform blood pressure calibration for each individual.

In particular, the calibrator 2 may be configured to perform measurement on blood pressure values based on Korotkoff sounds, and provide initial calibration parameters for calibrating the blood pressure measurement body 1 to the blood pressure measurement body 1.

The blood pressure measurement body 1 is configured to perform blood pressure measurement based on PPG, collect an ECG signal and a PPG signal, calibrate a PPG parameter-blood pressure equation based on the initial calibration parameters provided by the calibrator 2, and calculate the blood pressure value according to the PPG parameter-blood pressure equation.

More specifically, the blood pressure measurement body 1 may include an ECG acquisition device 11, a PPG acquisition device 12, a storage device 13, a first processor 14, a first communication device 15, and a watch wrap 16. The ECG acquisition device 11 is coupled to the first processor 14 and configured to collect and transmit an ECG signal to the first processor 14. The PPG acquisition device 12 is coupled to the first processor 14 and configured to collect and transmit a PPG signal to the first processor 14. Further, the PPG acquisition device 12 is configured to transmit PPG parameters corresponding to a cardiac cycle where a moment of the systolic pressure and a moment of the diastolic pressure fall within to the first processor 14.

Further, the storage device 13 is coupled to the first processor 14, and configured to store PPG parameters and the PPG parameter-blood pressure equation. The first processor 14 is configured to process the ECG signal and the PPG signal, calculate the systolic pressure and the diastolic pressure of the cardiac cycle where the a moment of systolic pressure notification signal and a moment of diastolic pressure notification signal fall within, and extract and calculate corresponding PPG parameters. Further, the first processor 14 is configured to transmit the PPG parameters corresponding to the cardiac cycle where a moment of the systolic pressure and a moment of the diastolic pressure fall within to the storage device 13. Further, according to the PPG parameter-blood pressure equation, the first processor 14 may calculate the blood pressure value.

Further, the first communication device 15 is coupled to the first processor 14, and is configured to receive a systolic pressure notification signal and a diastolic notification signal, the systolic pressure, and the diastolic pressure for calibration purpose. The systolic pressure notification signal and the diastolic notification signal, the systolic pressure, and the diastolic pressure for calibration purpose may be sent to the first communication device 15 by a second communication device 24 via the calibrator 2. The systolic pressure notification signal and the diastolic notification signal, the systolic pressure, and the diastolic pressure for calibration purpose may be the aforementioned initial calibration parameters.

The blood pressure measurement body 1 is configured to perform blood pressure measurement based on the PPG principle and thus can be used independently for blood pressure measurement. Further, the blood pressure measurement body 1 may be calibrated automatically any time. Here, the initial calibration parameters are only needed at a calibration moment, and when blood pressure measurement is performed independently at ordinary times, the blood pressure value may be calculated by using the PPG parameter-blood pressure equation after utilizing the PPG signal to calculate the PPG parameters. Further, the initial systolic pressure and the initial diastolic pressure involved in the PPG parameter-blood pressure equation are the systolic pressure and diastolic pressure in the initial calibration parameters provided by the calibrator 2.

Further, referring to FIG. 1, the calibrator 2 may include a sound transducer 21, a pressure gage 22, a second processor 23, a second communication device 24, and a cuff 25. In particular, the sound transducer 21 is configured to detect blood flow sound and convert the blood flow sound into an electric signal. The sound transducer 21 may further transmit the electric signal to the second processor 23. The pressure gage 22 is configured to measure a pressure inside the cuff 25. The second processor 23 is configured to process the electric signal and extract the Korotkoff sounds appeared in the blood flow sound and the pressure inside the cuff 25 at moments that the Korotkoff sounds correspond to the systolic pressure and the diastolic pressure.

In particular, the occurrence point of the Korotkoff sounds corresponds to the systolic pressure, and the vanishing point of the Korotkoff sounds corresponds to the diastolic pressure. Further, the second processor 23 controls the second communication device 24 to send out signals at the occurrence point and the vanishing point of the Korotkoff sounds, and more specifically, controls the second communication device 24 to send notification signals to the blood pressure measurement body 1, thereby recording the PPG parameters of the cardiac cycle where a current moment falls within.

Further, the second communication device 24 is coupled to the second processor 23, and configured to send a systolic pressure notification signal and a diastolic pressure notification signal, the systolic pressure, and the diastolic pressure to the blood pressure measurement body 1, respectively, at moments when the Korotkoff sounds correspond to the systolic pressure and the diastolic pressure. The calibrator 2 is configured to perform blood pressure measurement based on Korotkoff sounds, and provide initial reference data to calibrate the blood pressure measurement body 1 based on the PPG principle.

In particular, the second communication device 24 may be a receiving device has the same mode as, and a frequency point that matches the first communication device 15. Via the first communication device 15 and the second communication device 24, the calibrator 2 and the blood pressure measurement body 1 may perform information interaction with ease, thereby performing automatic calibration on the blood pressure measurement body 1.

Optionally, communications between the first communication device 15 and the second communication device 24 may include a wired method and a wireless method. The wireless method may include a Bluetooth method.

In one embodiment, in a blood pressure measurement device, the blood pressure measurement body 1 may be applied to PPG and ECG measurements during calibration and blood pressure detection anywhere and anytime after calibration. The calibrator 2 may be configured to calibrate the blood pressure measurement body 1 or occasionally measure the blood pressure at home.

As such, the present disclosure provides an auto-calibrated blood pressure measurement device based on the PPG principles. Under calibration, upon detection of the systolic pressure and the diastolic pressure, the calibrator 2 may send a signal to the blood pressure measurement body 1, and the blood pressure measurement body 1 may record the PPG parameters in a corresponding cardiac cycle after receiving the signal. The obtained systolic pressure, the diastolic pressure, and the PPG parameters may be substituted into the PPG parameter-blood pressure equation for calibration.

The calibration process of the PPG parameter-blood pressure equation may be completely automatically by the blood pressure measurement body 1. Further, the calibrated blood pressure measurement body 1 may measure the PPG parameters of the user and calculate the blood pressure value according to the calibration equation, thereby implementing accurate measurement of the blood pressure.

Embodiment 2

The present disclosure provides a calibration method based on the aforementioned blood pressure measurement device. The calibration method of the blood pressure measurement device may calibrate the blood pressure measurement device based on the PPG.

In the calibration method of the blood pressure measurement device, the calibrator 2 may send an notification signal to the blood pressure measurement body 1 when the systolic pressure and the diastolic pressure are detected according to the Korotkoff occurrence point and the Korotkoff vanishing point. After receiving an notification signal, the blood pressure measurement body 1 may calculate the cardiac cycle at a current moment and record the PPG parameter in the calculated cardiac cycle or average values of the PPG parameters in a plurality of cardiac cycles using the calculated cardiac cycle as a center. Further, the blood pressure measurement body 1 may utilize the systolic pressure and the diastolic pressure from the calibrator 2 and corresponding PPG parameters of the same cardiac cycle to update the PPG parameter-blood pressure equation, thereby improving the measurement precision of the blood pressure. In addition, the calibration of the PPG parameter-blood pressure equation may be completed automatically, thus making the regular calibration convenient and rapid.

Before calibration, the blood pressure measurement body 1 is placed on a limb of a tested user, and the calibrator 2 is placed on another limb of the tested user. As shown in FIG. 1, using the blood pressure measurement body 1 configured with the watch strap 16 and the calibrator 2 configured with the cuff 25 as an example, the blood pressure measurement body 1 may be put on an arm of the tested user first, and the cuff 25 of the calibrator 2 may be wrapped onto the upper arm of the tested user. Once the individual calibration keys for the blood pressure measurement body 1 and the calibrator 2 are pressed, respectively, the automatic calibration may be implemented. When in use, the pressure gage 22 may be configured inside the cuff 25 and holds an appropriate pressure with the cuff 25 and the upper arm, respectively. When not in use, the pressure gage 22 may move independently and freely with respect to the cuff 25.

Figure 2:
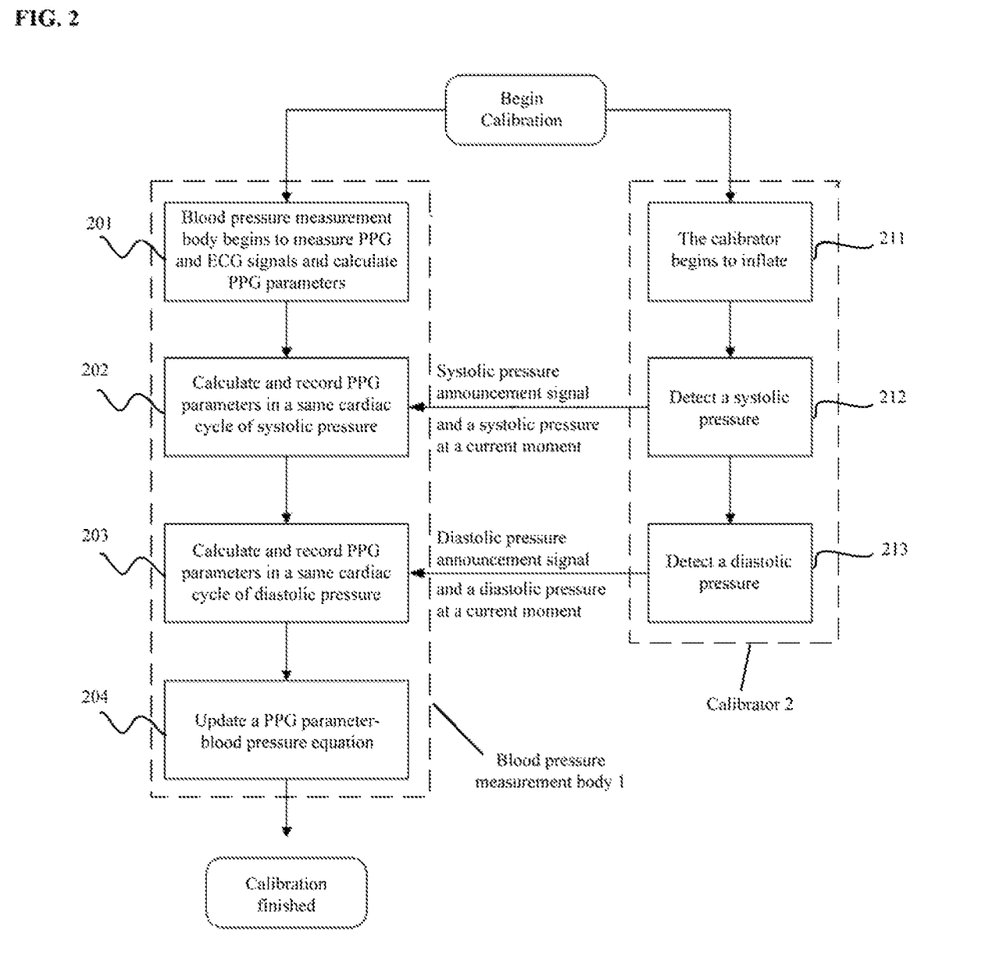
FIG. 2 is a diagram illustrating a flowchart of an exemplary calibration method of a blood pressure measurement device in some embodiments.

FIG. 2 is a diagram illustrating a flowchart of an exemplary calibration method of a blood pressure measurement device in some embodiments. As shown in FIG. 2, the calibration method of the blood pressure measurement device may include the following steps.

In step 201, after calibration, the blood pressure measurement body 1 may begin to measure the PPG and ECG signals and calculate the PPG parameters. The PPG parameters include a PPG transmission time and a peak-to-valley ratio.

Simultaneously, as shown in step 211, the calibrator 2 based on the Korotkoff sounds may start to inflate to perform blood pressure measurement. In step 212, the calibrator 2 may deflate, and when the systolic pressure is detected, the calibrator 2 may send a systolic notification signal and a systolic pressure at a first current moment to the blood pressure measurement body 1.

In step 202, after receiving the systolic pressure notification signal, the blood pressure measurement body 1 may determine the cardiac cycle that the first current moment belongs to and the blood measurement body 1 may calculate and record the PPG parameters in the same cardiac cycle of the systolic pressure. The PPG parameters may at least include the PPG transmission time.

In step 213, the calibrator 2 further deflates, and when the diastolic pressure is detected, the calibrator 2 may send a systolic notification signal and a systolic pressure at a second current moment to the blood pressure measurement body 1.

After receiving the systolic pressure notification signal, in step 203, the blood pressure measurement body 1 may determine the cardiac cycle that the second current moment belongs to, and calculate and record the PPG parameter in the same cardiac cycle of the systolic pressure. The PPG parameters include at least the PPG peak-to-valley ratio.

The blood pressure measurement body 1 may use the systolic pressure and the diastolic pressure received from the calibrator 2 as the initial systolic pressure and the initial diastolic pressure, respectively. Further, in step 204, according to the PPG transmission time and the PPG peak-to-valley ratio, the blood pressure measurement body 1 may update the PPG parameter-blood pressure equation.

In particular, the updated PPG parameter-blood pressure equation may be expressed as follows.

The systolic pressure: $SBP = a \cdot (x - x_0) + SBP_0$

The diastolic pressure:

$$DBP = b \cdot DBP_0 \cdot \frac{y_0}{y} + c$$

Where the $SBP_0$ is the initial systolic pressure received from calibrator 2, $x_0 = PTT_0$ or $x_0 = \overline{PTT}_0$, and $PTT_0$ and $\overline{PTT}_0$ are the initial PPG transmission time and the average initial PPG transmission time, respectively. Further, $x = PTT$ or $x = \overline{PTT}$, and PTT and $\overline{PTT}$ are the PPG transmission time and the average PPG transmission time, respectively, provided by the blood pressure measurement body 1, and a is a statistic constant.

$DBP_0$ is the initial diastolic pressure from the calibrator 2, $y_0 = PIR_0$, or $y_0 = \overline{PIR}_0$, $PIR_0$ and $\overline{PIR}_0$ are the initial PPG peak-to-valley ratio and the average initial PPG peak-to-valley ratio, respectively, $y = PIR$, or $y = \overline{PIR}$, and PIR and $\overline{PIR}$ are the PPG peak-to-ratio and the average PPG peak-to-ratio, respectively, provided by the blood pressure measurement body 1. Further, b and c are statistic constants.

The PPG transmission time may be a PPG transmission time in a single cardiac cycle, for example, $x_0 = PTT_0$ and $x = PTT$. The PPG peak-to-valley ratio may be a PPG peak-to-valley ratio in a single cardiac cycle, for example, $y_0 = PIR_0$ and $y = PIR$ To reduce the influence of the noise and improve the accuracy of the blood pressure measurement, the initial parameters of the systolic pressure and the diastolic pressure may use average values.

More specifically, the PPG transmission time may be an average PPG transmission time of a plurality of cardiac cycles including and using the current cardiac cycle as a center, for example, $x_0 = \overline{PTT}_0$, and $x = \overline{PTT}$ That is, the average value of the PPG parameters in three or five cardiac cycles may be recorded using the current cardiac cycle as a center (e.g., the average value of $PTT_0$ is $\overline{PTT}_0$). The PPG peak-to-valley ratio may be an average PPG peak-to-valley ratio in a plurality of cardiac cycles including and using the current cardiac cycle, such as $y_0 = \overline{PIR}_0$ and $y = \overline{PIR}$. That is, the average value of the PPG parameters in 3 or 5 cardiac cycles may be recorded using the current cardiac cycle as a center (e.g., the average of $PIR_0$ is $\overline{PIR}_0$).

At this point, the calibration is completed. Using the aforementioned equations of the systolic pressure and the diastolic pressure for calculating the systolic pressure and the diastolic pressure, the blood pressure measurement may become more accurate.

In particular, the limb of the tested user configured with blood pressure measurement body 1 may be a wrist, a finger, or an arm. For example, the disclosed blood pressure measurement body 1 may be placed on an upper arm. Further, the limb with the calibrator 2 may be an arm. For example, the calibrator 2 may be placed on another upper arm. The blood pressure measurement body 1 in the blood pressure measurement device may be configured in a plurality of measurement parts of the tested user, and the present disclosure is not intended to be limiting. Accordingly, the use of the blood pressure measurement device may be more convenient and flexible.

In the calibration method of the blood pressure measurement device, the communications between the blood pressure measurement body 1 and the calibrator 2 may include a wired or a wireless communication. The wireless communication may include a communication using Bluetooth. That is, via the first communication device 15 and the second communication device 24, the calibrator 2 and the blood pressure measurement body 1 may perform information interaction with ease, thereby performing automatic calibration on the blood pressure measurement body 1.

The present disclosure provides a calibration method of the blood pressure measurement device based on the PPG principle that can be automatically calibrated. When the calibrator 2 detects a systolic pressure (SBP0), the second communication device 24 may notify the blood pressure measurement body 1 via a wired or wireless (e.g., the Bluetooth) method. After receiving the signal, the first communication device 15 of the blood pressure measurement body 1 may transmit the signal to the first processor 14, and the first processor 14 may determine the specific cardiac cycle that the current moment belongs to. Further, the first processor 14 may transmit the calculated PPG parameters (e.g., the PPG transmission time $PTT_0$) in the cardiac cycle to the storage device 13 for record and storage, thereby implementing the measurement of the systolic pressure and the PPG parameters in the same cardiac cycle.

Further, as the cuff 25 deflates, when the calibrator 2 detects a systolic pressure (DBP0), the second communication device 24 may notify the blood pressure measurement body 1 via a wired or wireless communication method. After receiving the signal, the first communication device 15 of the blood pressure measurement body 1 may transmit the signal to the first processor 14, and the first processor 14 may determine the specific cardiac cycle that the current moment belongs to. Further, the first processor 14 may transmit the calculated PPG parameter (e.g., the PPG peak-to-valley ratio $PIR_0$) in the cardiac cycle to the storage device 13 for record and storage, thereby implementing the measurement of the systolic pressure and the diastolic pressure in the same cardiac cycle.

Further, the calibrator 2 may transmit the measured systolic pressure (SBP0) and the diastolic pressure (DBP0) to the blood pressure measurement body 1 via the second communication device 24. The blood pressure measurement body 1 may update the PPG parameter-blood pressure equation taking into account the PPG parameters ($PTT_0$ and $PIR_0$, or $\overline{PTT}_0$ and $\overline{PIR}_0$) corresponding to SBP0 and DBP0, respectively. After the calibration is completed, the calibrator 2 may no longer be needed, and the user may only need to wear the blood pressure measurement body 1 to independently measure the blood pressure of the user anywhere and anytime.

Figure 3:
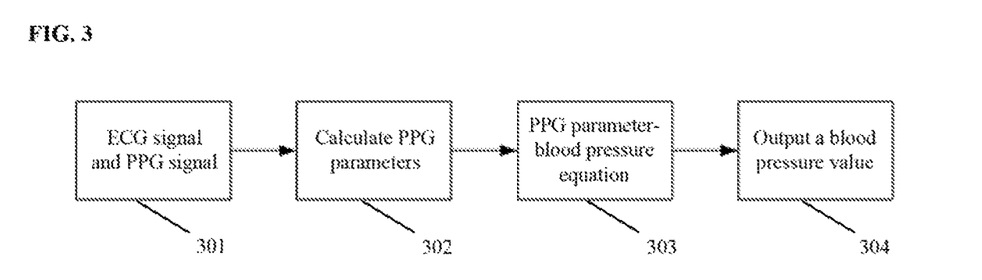
FIG. 3 is a diagram illustrating operational principles of an exemplary blood pressure measurement device in some embodiments.

FIG. 3 is a diagram illustrating operational principles of an exemplary blood pressure measurement device in some embodiments. A shown in FIG. 3, the blood pressure measurement body 1 may first measure the PPG signal and the ECG signal (301), and calculate the PPG parameters ($PTT_0$ and $PIR_0$, or $\overline{PTT}$ and $\overline{PIR}$) (302). Finally, the blood pressure measurement body 1 may substitute the parameters into the updated PPG parameter-blood pressure equation to calculate the blood pressure value (303). Finally, the blood pressure measurement body 1 may output a blood pressure value (304).

When the blood pressure measurement body 1 is used for a certain period of time (e.g., a few weeks) and the user needs to recalibrates the blood pressure measurement body 1, the calibration may be automatically completed with ease after the blood pressure measurement body 1 and the calibrator 2 are worn according to the aforementioned calibration steps and the calibration key is pressed.

In some embodiments, the blood pressure measurement body 1 and the calibrator 2 may execute the steps describe in relation to FIG. 2 multiple times during the calibration process. In some embodiments, if a user believes that the calibrator is not accurate, the blood pressure measurement body 1 may be disconnected from the first calibrator 2 and then connected to a second calibrator 2 to repeat the calibration process.

In some embodiments, the blood measurement body 1 may include a calendar stored in storage device 13. The blood measurement body 1 may be set a schedule to re-calibrate with calibrator 2 on a regular schedule, such as every month or every three months. The blood measurement body 1 may include a display device that can display a reminder for recalibration. For example, after the blood pressure measuring device is calibrated, the user may disconnect the calibrator 2 and only carries the blood measuring body 1 around. The blood measuring body 1 may prompt the user for re-calibration on its display device according to the calendar.

In some embodiments, the blood measurement device may include a wireless device, such as a Bluetooth device, that may connect to a computer, a smart phone, or another smart device. The blood measuring device may have a corresponding software application on the computer or smart phone. One of the functions (e.g., a push button) on the user interface of the application may be to calibrate blood pressure measurement body 1. A user may then start the calibration process though the user interface of the application, e.g., by clicking on the calibrate button in a smartphone application.

In some embodiments, a plurality of blood pressure measurement body 1 and calibrator 2 pairs may be monitored through a user application on a computer or a smart device. The first communication device and second commutation devices may establish a connection with the monitoring device. A user may start the calibration of the blood pressure measurement body 1 and monitor the process on the monitoring device. When the calibration process is complete, the user may then de-couple a pair of blood pressure measurement body 1 and calibrator 2. The calibrator 2 may then be used to couple with another blood pressure measurement body 1 to run the calibration steps again.

In some embodiments, the blood pressure measurement body 1 may be disconnected from the calibrator 2 after the calibration is completed. The blood pressure measurement body 1 may have a wired or wireless sensor to detect its connection with the calibrator 2. Once the calibrator 2 is re-connected to the blood pressure measurement body 1 through a wire or wireless connection, the blood pressure measurement body 1 may automatically rerun the calibration process.

In some embodiment, the blood pressure measurement body 1 may calibrate with calibrator 2 multiple times and record different PPG parameter-blood pressure equations. For example, a user may sit still during the first calibration process. The blood pressure measurement body 1 may record a first PPG parameter-blood pressure equation to correspond to a quiet state. The use may walk or move around during the second calibration process. The blood pressure measurement body 1 may record a second PPG parameter-blood pressure equation to correspond to a moving state. The blood pressure measurement body 1 may further include a motion sensor. Depending the reading from the motion sensor, the blood pressure measurement body 1 may determine whether the user is in a quiet state or a moving state. The blood pressure measurement body 1 may then use the PPG parameter-blood pressure equation corresponding to the specific state to calculate the measured blood pressure.

It should be understood that the aforementioned embodiments are merely exemplary embodiments used to illustrate the principles of the present disclosure, and the present disclosure is not limited thereto. For those ordinarily skilled in the art, without departing from the spirit and scope of the present disclosure, various alterations and modifications may be made, and these alterations and modifications all fall within the scope of the present disclosure.

What is claimed is:

1. A blood pressure measurement device, comprising:
a blood pressure measurement body configured to determine blood pressure based on photoplethysmogram (PPG); and
a calibrator configured to measure blood pressure values based on Korotkoff sounds,
wherein the calibrator is further configured to provide initial calibration parameters to the blood pressure measurement body, and
the blood pressure measurement body is further configured to collect an electrocardiogram (ECG) signal and a PPG signal, update a PPG parameter-blood pressure equation according to the initial calibration parameters to obtain an updated PPG parameter-blood pressure equation, and calculate a blood pressure value according to the updated PPG parameter-blood pressure equation;
wherein the updated PPG parameter-blood pressure equation comprises:

$$SBP = a \cdot (x - x_0) + SBP_0; \text{ and}$$

$$DBP = b \cdot DBP_0 \cdot \frac{y_0}{y} + c;$$

wherein SBP stands for systolic pressure; $SBP_0$ is an initial systolic pressure; $x_0 = PTT_0$ or $x_0 = \overline{PTT_0}$; $PTT_0$ and $\overline{PTT_0}$ are an initial PPG transmission time and an average initial PPG transmission time, respectively; $x = PTT$, or $x = \overline{PTT}$, PTT and $\overline{PTT}$ are a PPG transmission time and an average PPG transmission time, respectively; and a is a statistic constant, and DBP stands for diastolic pressure; $DBP_0$ is an initial diastolic pressure; $y_0 = PIR_0$ or $y_0 = \overline{PIR_0}$; $PIR_0$ and $\overline{PIR_0}$ are an initial PPG peak-to-valley ratio and an average initial PPG peak-to-valley ratio, respectively; $y = PIR$ or $y = \overline{PIR}$, PIR and $\overline{PIR}$ are a PPG peak-to-ratio and an average PPG peak-to-ratio, respectively; and b and c are statistic constants.

2. The blood pressure measurement device according to claim 1, wherein:

the blood pressure measurement body further includes an ECG acquisition device, a PPG acquisition device, a storage device, a first processor, and a first communication device;

the ECG acquisition device is coupled to the first processor, and configured to collect and transmit the ECG signal to the first processor;

the PPG acquisition device is coupled to the first processor, and configured to collect and transmit the PPG signal to the first processor;

the storage device is coupled to the first processor, and configured to store a PPG parameter and the updated PPG parameter-blood pressure equation; and the first processor is configured to process the ECG signal and the PPG signal, extract and calculate the PPG parameter in a cardiac cycle when receiving a systolic pressure notification signal and when receiving a diastolic pressure notification signal, transmit the PPG parameter of the cardiac cycle, and calculate the blood pressure value according to the updated PPG parameter-blood pressure equation.

3. The blood pressure measurement device according to claim 2, wherein:

the calibrator includes a cuff, a sound transducer, a pressure gage, a second processor, and a second communication device, the sound transducer is configured to detect and convert a blood flow sound to an electric signal, the pressure gage is configured to measure a pressure inside the cuff, the second processor is configured to process the electric signal, and extract the Korotkoff sounds appeared in a blood flow sound and the pressure inside the cuff at instances that the Korotkoff sounds correspond to the systolic pressure and the diastolic pressure, and the second communication device is coupled to the second processor, and configured to send a systolic pressure notification signal and a diastolic pressure notification signal, the systolic pressure and the diastolic pressure to the blood pressure measurement body, respectively, at moments that the Korotkoff sounds correspond to the systolic pressure and the diastolic pressure.

4. The blood pressure measurement device according to claim 3, wherein:

the second communication device includes a receiving device that matches with the first communication device.

5. The blood pressure measurement device according to claim 4, wherein:

communications between the first communication device and the second communication device include a wired communication or a wireless communication.

6. The blood pressure measurement device according to claim 1, wherein:

the blood pressure measurement body is further configured to perform calibration based on blood pressure values based on Korotkoff sounds.

7. The blood pressure measurement device according to claim 1, wherein:

the $PTT_0$ is derived based on a first initial ECG signal and a second initial PPG signal in a same cardiac cycle during which the $SBP_0$ is measured; and the $PIR_0$ is derived based on a third initial ECG signal and a fourth initial PPG signal in a same cardiac cycle during which the $DBP_0$ is measured.

8. A calibration method of a blood pressure measurement device, comprising:

measuring a photoplethysmogram (PPG) signal and an electrocardiogram (ECG) signal and calculating PPG parameters, by a blood pressure measurement body, wherein the PPG parameters include a PPG transmission time and a PPG peak-to-valley ratio;

inflating a calibrator;

deflating the calibrator, and when a systolic pressure is detected, sending a systolic pressure notification signal and a systolic pressure at a first instance to the blood pressure measurement body;

after receiving, by the blood pressure measurement body, the systolic pressure notification signal, determining a cardiac cycle that the first instance belongs to, and calculating and recording the PPG parameters in a same cardiac cycle as the systolic pressure, wherein the PPG parameters at least include the PPG transmission time;

when a diastolic pressure is detected, sending a diastolic pressure notification signal and a diastolic pressure at a second instance to the blood pressure measurement body;

after receiving, by the blood pressure measurement body, the diastolic pressure notification signal, determining the cardiac cycle that the second instance belongs to, and calculating and recording the PPG parameters in the same cardiac cycle as the diastolic pressure, wherein the PPG parameters at least include the PPG peak-to-valley ratio, and updating a PPG parameter-blood pressure equation according to the PPG transmission time and the PPG peak-to-valley ratio; and wherein the systolic pressure is determined as: $SBP = a \cdot (x - x_0) + SBP_0$, and the diastolic pressure is determined as:

$$DBP = b \cdot DBP_0 \cdot \frac{y_0}{y} + c;$$

wherein $SBP_0$ is an initial systolic pressure; $x_0 = PTT_0$ or $x_0 = \overline{PTT}_0$; $PTT_0$ and $\overline{PTT}_0$ are an initial PPG transmission time and an average initial PPG transmission time, respectively; $x = PTT$, or $x = \overline{PTT}$, $PTT$ and $\overline{PTT}$ are a PPG transmission time and an average PPG transmission time, respectively; and a is a statistic constant, and $DBP_0$ is an initial diastolic pressure; $y_0 = PIR_0$ or $y_0 = \overline{PIR}_0$; $PIR_0$ and $\overline{PIR}_0$ are an initial PPG peak-to-valley ratio and an average initial PPG peak-to-valley ratio, respectively; $y = PIR$ or $y = \overline{PIR}$, $PIR$ and $\overline{PIR}$ are a PPG peak-to-ratio and an average PPG peak-to-ratio, respectively; and b and c are statistic constants.

9. The calibration method according to claim 8, wherein:

the $PTT_0$ is derived based on a first initial ECG signal and a second initial PPG signal in a same cardiac cycle during which the $SBP_0$ is measured; and the $PIR_0$ is derived based on a third initial ECG signal and a fourth initial PPG signal in a same cardiac cycle during which the $DBP_0$ is measured.

10. The calibration method according to claim 8, wherein:

the PPG transmission time is a PPG transmission time in a single cardiac cycle, or an average value of PPG transmission time in a plurality of cardiac cycles, and the PPG peak-to-valley ratio is a PPG peak-to-valley ratio in a single cardiac cycle, or an average value of PPG peak-to-valley ratios in a plurality of cardiac cycles.

11. The calibration method according to claim 8, wherein:
a limb of a tested user where the blood pressure measurement body is placed is a wrist, a finger, or an arm, and another limb of the tested user where the calibrator is placed is an arm.

12. The calibration method according to claim 8, wherein:
communications between the blood pressure measurement body and the calibrator include a wired communication or a wireless communication.

13. A calibration method of a blood pressure measurement device, comprising:
measuring a photoplethysmogram (PPG) signal and an electrocardiogram (ECG) signal and calculating PPG parameters, by a blood pressure measurement body, wherein the PPG parameters include a PPG transmission time and a PPG peak-to-valley ratio;
when a systolic pressure is detected by a calibrator, receiving a systolic pressure notification signal and a systolic pressure at a first instance;
determining a cardiac cycle that the first instance belongs to, and calculating and recording the PPG parameters in a same cardiac cycle as the systolic pressure, wherein the PPG parameters at least include the PPG transmission time;
when a diastolic pressure is detected by the calibrator, receiving a diastolic pressure notification signal and a diastolic pressure at a second instance;
determining the cardiac cycle that the second instance belongs to, and calculating and recording the PPG parameters in the same cardiac cycle as the diastolic pressure, wherein the PPG parameters include the PPG peak-to-valley ratio, and
updating a PPG parameter-blood pressure equation according to the PPG transmission time and the PPG peak-to-valley ratio; and
wherein the systolic pressure is determined as: $SBP = a \cdot (x - x_0) + SBP_0$, and the diastolic pressure is determined as:

$$DBP = b \cdot DBP_0 \cdot \frac{y_0}{y} + c;$$

wherein $SBP_0$ is an initial systolic pressure; $x_0 = PTT_0$ or $x_0 = \overline{PTT}_0$; $PTT_0$ and $\overline{PTT}_0$ are an initial PPG transmission time and an average initial PPG transmission time, respectively; $x = PTT$, or $x = \overline{PTT}$, $PTT$ and $\overline{PTT}$ are a PPG transmission time and an average PPG transmission time, respectively; and a is a statistic constant, and $DBP_0$ is an initial diastolic pressure; $y_0 = PIR_0$ or $y_0 = \overline{PIR}_0$; $PIR_0$ and $\overline{PIR}_0$ are an initial PPG peak-to-valley ratio and an average initial PPG peak-to-valley ratio, respectively; $y = PIR$ or $y = \overline{PIR}$, $PIR$ and $\overline{PIR}$ are a PPG peak-to-ratio and an average PPG peak-to-ratio, respectively; and b and c are statistic constants.

14. The calibration method according to claim 13, wherein:
the $PTT_0$ is derived based on a first initial ECG signal and a second initial PPG signal in a same cardiac cycle during which the $SBP_0$ is measured; and
the $PIR_0$ is derived based on a third initial ECG signal and a fourth initial PPG signal in a same cardiac cycle during which the $DBP_0$ is measured.

15. The calibration method according to claim 13, wherein:
the PPG transmission time is a PPG transmission time in a single cardiac cycle, or an average value of PPG transmission time in a plurality of cardiac cycles, and
the PPG peak-to-valley ratio is a PPG peak-to-valley ratio in a single cardiac cycle, or an average value of PPG peak-to-valley ratios in a plurality of cardiac cycles.

* * * * *